(12) United States Patent
Rigdon et al.

(10) Patent No.: US 6,310,253 B1
(45) Date of Patent: Oct. 30, 2001

(54) PREPARATION OF 1,3,5-TRIAMINO-2,4,6-TRINITROBENZENE OF SUBMICRON PARTICLE SIZE

(75) Inventors: Lester P. Rigdon, Livermore; Gordon L. Moody, Tracy; Raymond R. McGuire, Brentwood, all of CA (US)

(73) Assignee: The United States of America as represented by the Department of Energy, Washington, DC (US)

( * ) Notice: Subject to any disclaimer, the term of this patent is extended or adjusted under 35 U.S.C. 154(b) by 0 days.

(21) Appl. No.: 06/754,896

(22) Filed: May 22, 1985

(51) Int. Cl.$^7$ .................. C07C 211/52; C06B 21/00
(52) U.S. Cl. .................. 564/441; 149/109.6; 564/437
(58) Field of Search .................. 149/92, 105, 109.6; 564/437, 438, 441

(56) References Cited

U.S. PATENT DOCUMENTS

| | | | |
|---|---|---|---|
| 3,301,904 | * 1/1967 | Cryer | 564/438 |
| 3,715,398 | * 2/1973 | Kaufman | 564/437 |
| 3,985,595 | * 10/1976 | Benziger | 149/105 |
| 4,032,377 | * 6/1977 | Benziger | 149/105 |
| 4,180,424 | * 12/1979 | Reed et al. | 149/19.1 |
| 4,248,798 | * 2/1981 | Atkins et al. | 564/441 |
| 4,255,358 | * 3/1981 | Jones et al. | 149/105 |
| 4,439,622 | * 3/1984 | Hansen et al. | 564/406 |
| 4,481,371 | * 11/1984 | Benziger | 149/92 |
| 4,554,031 | * 11/1985 | Kerviel et al. | 149/105 |
| 4,564,405 | * 1/1986 | Pallanck | 149/92 |
| 4,604,489 | * 8/1986 | Kayser | 568/931 |

* cited by examiner

*Primary Examiner*—Edward A. Miller
(74) *Attorney, Agent, or Firm*—L. E. Carnahan; Henry P. Sartorio; Paul A. Gottlieb

(57) ABSTRACT

A method is disclosed for the preparation of very small particle size, relatively pure 1,3,5-triamino-2,4,6-trinitrobenzene (TATB). Particles of TATB prepared according to the disclosed method are of submicron size and have a surface area in the range from about 3.8 to 27 square meters per gram.

9 Claims, 1 Drawing Sheet

PREPARATION OF 1,3,5-TRIAMINO-2,4,6-TRINITROBENZENE OF SUBMICRON PARTICLE SIZE

The United States Government has rights in this invention pursuant to Contract No. W-7405-ENG-48 between the United States Department of Energy and the University of California for the operation of the Lawrence Livermore National Laboratory.

This invention is in the general area of explosive compounds and more particularly, in the area of highly insensitive, heat resistant nitro-organic explosives.

BACKGROUND OF THE INVENTION

In recent times, 1,3,5-triamino-2,4,6-trinitro-benzene (TATB) has been in great demand as an explosive in some applications because of its high resistance to shock (insensitivity), its stability, its high density and its accelerated detonation characteristics relative to other conventional explosives such as TNT. A few methods for the preparation of diamino-trinitro-benzene, TATB or TATB-based explosives have been published.

U.S. Pat. No. 4,248,798, issued to Atkins et al., teaches a method for preparing penta-nitro-aniline and triamino-trinitro-benzene from trinitro-toluene.

U.S. Pat. No. 4,439,622, issued to Hansen et al., discloses a method of forming large crystals of 1,3,5-triamino-trinitro-benzene by aminating 1,3,5-trichloro-trinitro-benzene with a suitable aminating agent.

U.S. Pat. No. 3,985,595, issued to Benziger, discloses an insensitive plastic-bonded explosive consisting of a mixture of 90 wt % of triamino-trinitrobenzene and 10 wt % of a saturated copolymer of chloro-trifluoro-ehtylene and vinylidene fluoride and a method for its preparation.

In some instances, very fine particle size material with a surface area of the order of several square meters per gram is desirable. Normally, with most chemicals, small particle size material may be obtained by conventional purification methods known in the art such as precipitation, coprecipitation and the like. However, controlling the particle size or producing TATB of sub-micron particle size by the use of these conventional methods has not been heretofore possible because suitable solvents and techniques have not been available.

U.S. Pat. No. 4,032,377, ('377 patent), issued to Benziger, describes a method for the production of high-purity triamino-trinitro-benzene whereby 1,3,5-trichloro-benzene is nitrated to form 1,3,5-trichloro-2,4,6-trinitro-benzene followed by amination to triamino-trinitro-benzene in the presence of sufficient water to render the ammonium chloride byproduct semideliquescent. However, the '377 patent does not refer to any particle size desirable or achieved.

It would be desirable, therefore, to have available a method for the production of TATB of small particle size.

Accordingly, it is an object of the subject invention to provide an explosive composition with improved detonating characteristics.

Yet another object is to provide TATB of a high degree of purity and of small particle size.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention as embodied and broadly described herein, the present invention is directed to a method for the preparation of very small particle size, high purity 1,3,5-triamino-2,4,6-trinitrobenzene, TATB. One preferred embodiment of the subject method comprises dissolving TATB, obtained either commercially or prepared in the laboratory by known methods, in a suitable solvent, most preferably, dimethyl-sulfoxide (DMSO), making the solution alkaline by the addition of a suitable alkali to dissolve all of the TATB, completely neutralizing the solution by the addition of a suitable acid (when fine crystals of TATB product separate out), and collecting and washing the crystals. Suitable alkalis include but are not limited to sodium hydroxide, potassium hydroxide, ammonia solution, and the like. Suitable acids include but are not limited to mineral acids such as nitric acid, sulfuric acid, and hydrochloric acid.

The desired particle size of TATB may be varied by varying the concentration of the aqueous acid solution used and also by varying the rate and manner of mixing the components. Typically, a larger surface area is obtained by rapidly adding the TATB solution to a very dilute solution of the acid. Pipetting a solution of the acid into a moderately stirred solution of TATB yields a product with larger particle size.

According to another embodiment of the instant invention, commercially obtained TATB is dissolved in a suitable solvent such as DMSO, when the solution is heated to a temperature of about 180° C. to about 195° C., most preferably from about 182° C. to about 185° C., while vigorously stirring it to dissolve all of the TATB. The hot TATB solution is then delivered into vigorously stirred cold water and the solution allowed to cool as fine crystals of TATB product separate out. The crystals are collected and washed to remove residual solvent and other impurities that may be present.

DETAILED DESCRIPTION OF THE INVENTION

Figure 1:
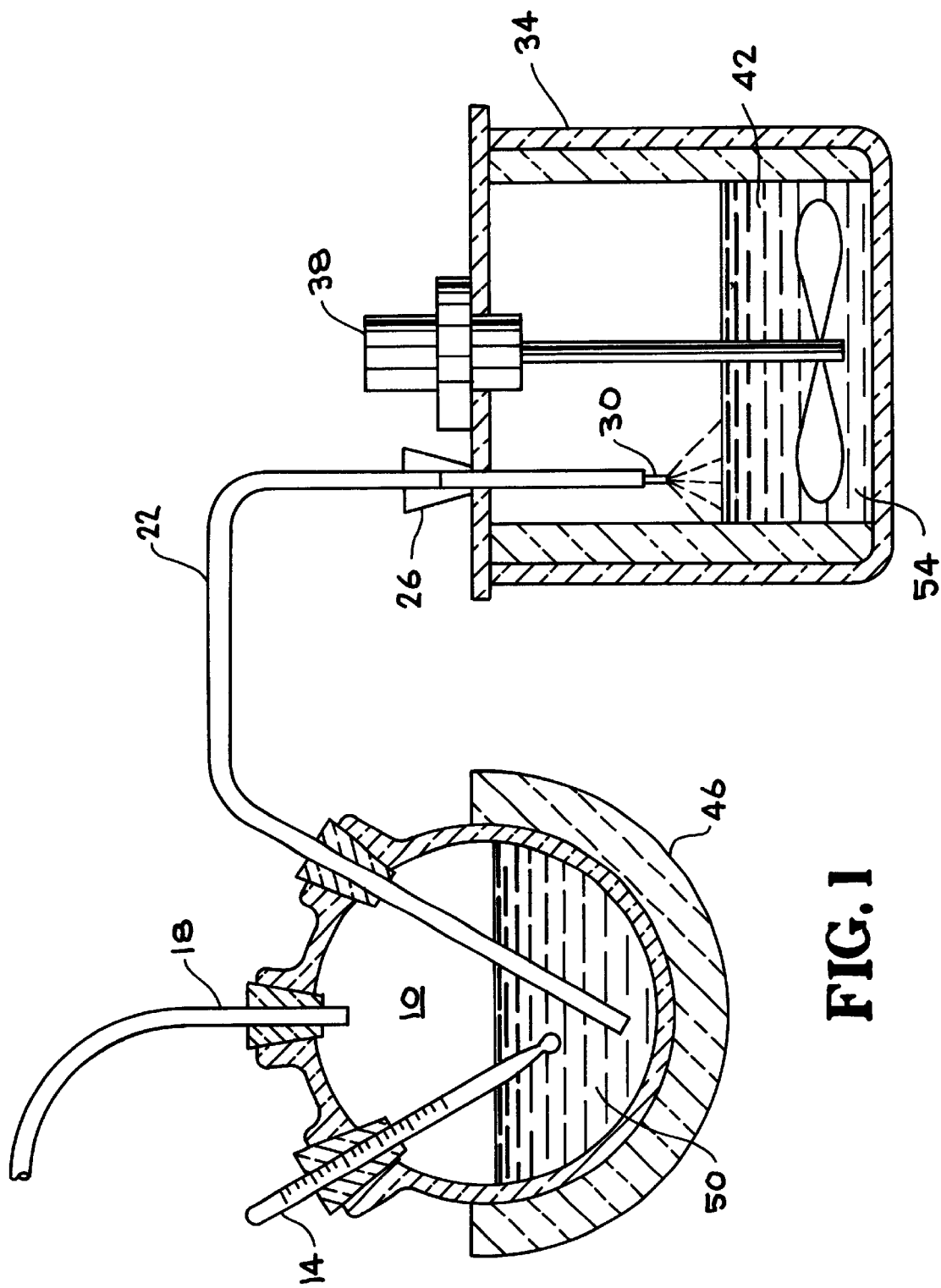
FIG. 1 is a diagram of one type of apparatus that can be used for the practice of the subject invention.

The basis of the instant invention is the production of TATB in sub-micron, highly amorphous crystallites. The instant invention is thus directed to a method for the preparation of very small particle size, preferably, submicron particle size, from about 0.2 to 0.3 microns in diameter, with surface areas greater than 3 $m^2/gm$, of relatively pure TATB. The surface area may be varied by adjusting precipitation conditions and procedures. Two factors that are crucial to the present invention are 1) dissolution of the TATB in sufficient quantities and 2) precipitating it out of solution to remove impurities and to control the particle size. According to one aspect of the present invention, the dissolution process is accomplished by the use of a combination of DMSO and an alkali such as sodium hydroxide, potassium hydroxide, lithium hydroxide and the like; or by employing DMSO alone at elevated temperatures, 182° to 185° C. being most suitable. Sodium hydroxide is the most preferred alkali. The precipitation of the TATB is achieved by injecting or spraying the TATB solution into vigorously stirred dilute mineral acid if DMSO and alkali are used for the dissolution process and into vigorously stirred cold water if hot DMSO is employed for the dissolution. As used herein, "TATB product" refers to the pure, fine particle size TATB obtained by the methods disclosed and claimed herein.

In one preferred embodiment of the present invention, TATB of the desired purity and small particle size can be prepared by dissolving a suitable amount of commercially obtained TATB, preferably about 2.5 wt % of TATB, or about 0.1 moles of TATB in DMSO, preferably in an inert atmosphere. Sufficient sodium hydroxide is then added to dissolve completely any residual TATB. Once the dissolution is completed, the resulting mixture is then either sprayed or injected into a suitable reaction vessel containing sufficient dilute nitric acid in water to neutralize the amount of sodium hydroxide used in the dissolution process. The reaction mixture is vigorously stirred as it is sprayed or injected. The precipitated or condensed particles of the TATB product which are now very small and pure, are collected, washed and dried.

The particle size of TATB may be varied by varying the concentration of the aqueous acid solution used and also by varying the rate and manner of mixing the components. Typically, a larger surface area is obtained by rapidly adding the TATB solution to a very dilute solution of the acid. Pipetting a solution of the acid into a moderately stirred solution of TATB yields a product with larger particle size.

According to another embodiment of the instant invention, a suitable amount of TATB is dissolved in a suitable solvent such as DMSO, and the solution is heated to a temperature in the range of from about 180° C. to about 185° C., preferably from about 182° C. to about 185° C., while vigorously stirring it to dissolve all of the TATB. The hot TATB solution is then delivered into vigorously stirred cold water and the solution allowed to cool when fine crystals of TATB product separate out. The crystals are collected and washed to remove residual solvent and other impurities that may be present. Surface areas for TATB product prepared in accordance with the present invention range from about 3.8 to about 27 $m^2/gm$.

FIG. 1 is a schematic diagram of the apparatus used to prepare very small particle size TATB of high purity, prepared in accordance with one preferred embodiment of the instant invention. A round bottomed flask 10 is fitted with a thermometer 14, a ground glass taper 18 for supplying an inert gas such as argon, a sparger system 22 fitted with ground glass taper fitting 26 and spray nozzle 30 at one end. Fitting 26 and nozzle 30 are attached to slurry reactor 34 which is provided with an air motor drive 38 to keep the cold water, and crash precipitate solution 42 stirred. Flask 10 is also provided with a heating mantle 46 to heat the TATB solution 50. TATB and DMSO solvent are charged to flask 10 and the solution is heated to no more than about 185° C., preferably to about 182° C. Once TATB is completely dissolved, the solution is driven out of flask 10 by means of an inert gas such as argon pumped in through ground glass fitting 18, at a presuure of approximately 1 psi, into sparger system 22, and is sprayed through nozzle 30 into reactor 34 containing cold water that is vigorously stirred by motor 38. TATB precipitate 54 is then collected and washed.

Two methods for dissolving up to about 5 gms or 0.02 moles of TATB per liter of solvent are described in the examples below. These examples serve to illustrate the instant invention and are not to be construed as limiting the invention to the precise form described or limiting it in any other manner.

EXAMPLE 1

TATB was obtained commercially from Hercules Company, McGregor, Tex. and was used without prior purification. 5 grams (about 0.02 moles) of the TATB was charged into a round bottomed flask equipped with a stirrer. 200 ml of dimethylsulfoxide (DMSO) was added to the reaction vessel. The mixture was stirred vigorously while enough sodium hydroxide solution was added until a molar ratio of 1.5:1 of NaOH/TATB was achieved (about 1.16 grams of NaOH). Stirring was continued until all of the TATB was dissolved, as observed by the disappearance of the particles of TATB and the appearance of a clear red solution. TATB was precipitated by mixing the solution with an aqueous solution of nitric acid at a molar ratio of 1.03:1 of nitric acid to sodium hydroxide. Injecting a very fine spray of TATB solution into a vigorously stirred solution of 0.06M nitric acid, using the apparatus shown in FIG. 1, yielded TATB of a fine particle size with the largest surface area per gram, whereas pipetting a 2M solution of nitric acid into a moderately-stirred solution of TATB yielded a product with the smallest surface area of about 3.8 $m^2/gm$. The resultant precipitate was filtered and washed several times with deionized water to remove residual solvent and other impurities. The final material was then collected on a filter. This product was of very small particle size with large surface area per unit weight, typically in the range of about 4 to about 15 $m^2/gm$.

EXAMPLE 2

5 gram of the commercially obtained TATB was mixed with 200 ml of DMSO in a dissolution vessel. The reaction vessel was placed in a heating mantle or other suitable heating apparatus and heated while stirring vigorously until the TATB is dissolved and the temperature of the solution rises to about 182–185° C. Transfer tube 10, shown in FIG. 1 was heated to a temperature in the range of from about 185° C. to about 190° C. The tip of the delivery tube was placed about 1 inch from a precipitation vessel containing at least twice as much of deionized cold water as the volume of hot DMSO solution. The cold water was vigorously stirred and while still being so stirred, the hot DMSO solution was delivered into the cold water. The resulting solution was allowed to cool to ambient temperature and the contents filtered and washed several times with deionized water to remove residual solvent and other impurities. The resulting TATB is yellow in color, and is a material of high purity and small particle size with a large surface area per unit weight.

TATB produced in accordance with the procedure described herein and in the disclosed form has the peculiar property of being quite sensitive to very high amplitude shock waves of very short duration while being at least as insensitive as normal TATB to other stimuli such as normal shock loading, thermal stimuli, friction impact and the like. These short pulses are normally generated by electronically driven plastic flyers ("Slappers").

This characteristic of sensitivity makes it possible to build a super safe explosive end use having all "Insensitive High Explosive (IHE)". Thus, there would be no sensitive or hazardous explosive even in the detonator train.

The above embodiments were chosen and described in order to explain best the principles and the practical applications of the subject invention thereby to enable those skilled in the art to utilize the invention in various other embodiments and various modifications as are suitable for the particular use contemplated. The foregoing description of one preferred embodiments of the invention, therefore, has been presented only for purposes of description and illustration of the subject invention. It is not intended to be exhaustive or to limit the invention to the precise forms disclosed, and many modifications and variations thereof would become obvious to those skilled in the art from the teachings and disclosure herein. It is intended that the scope of the invention is best defined by the appended claims.

What is claimed is:

1. A method for preparing very small particle size, high purity TATB, comprising:

mixing commercially obtained TATB with a suitable solvent;

adding enough alkali to the mixture to completely dissolve said TATB;

adding to said mixture an aqueous solution of a suitable acid to neutralize any remaining alkali;

collecting the resultant precipitate of the TATB product; and washing said precipitate several times with deionized water to remove solvent and impurities.

2. The method of claim 1 wherein said solvent is dimethylsulfoxide.

3. The method of claim 1 wherein said alkali is selected from a group consisting of sodium hydroxide, potassium hydroxide and lithium hydroxide.

4. The method of claim 3 wherein said alkali is sodium hydroxide.

5. The method of claim 1 wherein said acid is selected from a group consisting of sulfuric acid, hydrochloric acid and nitric acid.

6. The method of claim 5 wherein said solvent is dimethylsulfoxide, said alkali is sodium hydroxide and said acid is nitric acid.

7. The method of claim 6 wherein the molar ratio of said sodium hydroxide to TATB in the mixture is about 1.5:1.

8. The method of claim 7 wherein the surface area of said TATB is greater than 3.5 $m^2$/gm.

9. The method of claim 8 wherein the surface area of said TATB is in the range of from about 3.8 to 27 $m^2$/gm.

* * * * *